(12) United States Patent
Li et al.

(10) Patent No.: US 10,022,046 B2
(45) Date of Patent: Jul. 17, 2018

(54) MULTI-CHANNEL OPTICAL COHERENCE TOMOGRAPHY PROBE FOR USE IN A MEDICAL PROCEDURE

(71) Applicants: Fangxin Li, Toronto (CA); Michael Frank Gunter Wood, Toronto (CA)

(72) Inventors: Fangxin Li, Toronto (CA); Michael Frank Gunter Wood, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

(21) Appl. No.: 15/107,484

(22) PCT Filed: Sep. 2, 2015

(86) PCT No.: PCT/IB2015/056669
§ 371 (c)(1),
(2) Date: Jun. 23, 2016

(87) PCT Pub. No.: WO2017/037506
PCT Pub. Date: Mar. 9, 2017

(65) Prior Publication Data
US 2017/0202452 A1    Jul. 20, 2017

(51) Int. Cl.
*A61B 5/05* (2006.01)
*A61B 3/10* (2006.01)

(52) U.S. Cl.
CPC .................................. *A61B 3/102* (2013.01)

(58) Field of Classification Search
CPC .............................. A61B 6/032; A61B 6/504
See application file for complete search history.

(56) References Cited

U.S. PATENT DOCUMENTS

| | | | |
|---|---|---|---|
| 7,102,746 B2 | 9/2006 | Zhao | |
| 2010/0168586 A1* | 7/2010 | Hillman | G02B 23/2476 600/476 |
| 2013/0023760 A1* | 1/2013 | Liu | A61B 5/6852 600/425 |
| 2014/0221826 A1* | 8/2014 | Joos | A61B 5/0066 600/425 |

FOREIGN PATENT DOCUMENTS

EP    1929939 A2    6/2008

OTHER PUBLICATIONS

Oprea, Karen. "International Search Report." PCT International Application No. PCT/IB2015/056669 dated Jun. 1, 2016.

* cited by examiner

*Primary Examiner* — Hien Nguyen
(74) *Attorney, Agent, or Firm* — Perry + Currier Inc.

(57) ABSTRACT

A multi-channel optical coherence tomography probe for use in a medical procedure is provided. The probe comprises: a plurality of first optical fibers optically connectable to an OCT light source; a plurality of second optical fibers different from the plurality of first optical fibers; a scanning device comprising: an actuator configured to rotationally move the plurality of second optical fibers between a first position and a second position, relative to the plurality of first optical fibers; and, a mirror configured to, as the plurality of second optical fibers is moving rotationally, convey light from exit faces of the plurality of first optical fibers to entrance faces of the plurality of second optical fibers; and, a housing containing the plurality of second optical fibers.

14 Claims, 12 Drawing Sheets

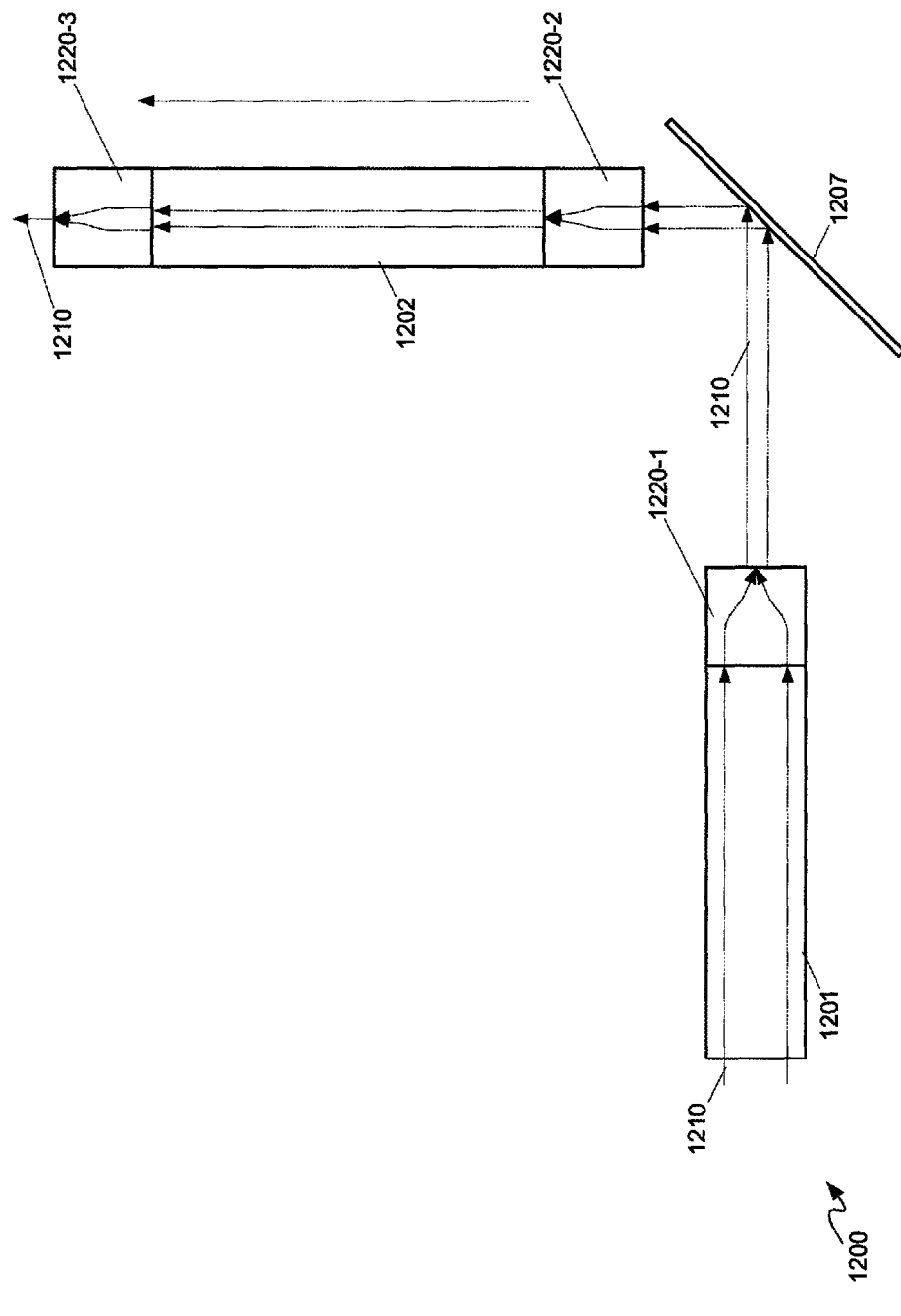

MULTI-CHANNEL OPTICAL COHERENCE TOMOGRAPHY PROBE FOR USE IN A MEDICAL PROCEDURE

FIELD

The specification relates generally to optical coherence tomography probes and methods for minimally invasive therapy and image guided medical procedures, and specifically to multi-channel Optical Coherence Tomography (OCT) probe for use in a medical procedure.

BACKGROUND

Fourier domain optical coherence tomography (OCT), which employs the wavelength swept fiber laser source can be the most suitable OCT system for commercial purposes in biomedical imaging. Standard swept source OCT system generally requires some scanning mechanism for three-dimensional imaging to provide high resolution, high sensitivity, and cost-effective system. However, for some applications, the scanning swept source OCT may not be suitable due to the following issues.

First, imaging speed has a fundamental significance not only because of the high demanding of real-time information, but its relationship to detection sensitivity (e.g. minimum detectable reflectivity). The scanning OCT obtains a three-dimensional image with point to point scanning, and thus provides slower imaging speed than full-field OCT system. In order to increase the imaging speed, a more complicate and expensive high-speed tunable laser can be used. Moreover, as an A-line rate increases, detection bandwidth is generally increased proportionally, and therefore the sensitivity drops. Although increasing the laser source power would, in principle, improve the sensitivity, available laser sources and maximum permissible exposure levels of tissue represent significant practical limitations.

Second, a maximum imaging depth in tissues of all OCT is limited to a few millimeters due to the absorption and scattering of biological tissue. Consequently, a passive probe for endoscopic OCT imaging is highly desired. Currently, most scanning probes in OCT systems can be divided into two categories: I) probes using MEMS (microelectromechanical systems) mirror for front view two-dimensional scans; and II) probes using a rotating mechanism for lateral view two-dimensional scans. Using MEMS mirrors can more suitable for brain imaging where front view is preferred. However, rotating MEMS mirror at a distal end of an OCT probe means that every OCT probe using a MEMS mirror has its own scanning system. When such OCT scanning probes are meant to be disposable, the cost can be too high to justify such disposal and yet there may be no choice but to dispose to prevent cross-contamination of patients. Furthermore, parallel probes using MEMS mirrors can further require sophisticated engineering, which can prevent their use with real-time imaging systems.

SUMMARY

The present disclosure is generally directed to image guided medical procedures which may or may not use an access port. A port-based surgery approach allows a surgeon, or robotic surgical system, to perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

Furthermore, a multi-channel OCT (Optical Coherence Tomography) probe, for use in a medical procedure, is provided which includes a plurality of first optical fibers having a fixed position relative to an OCT light source, and a plurality of second optical fibers different from the plurality of first optical fibers. A scanning device is also provided which includes an actuator configured to rotationally move the plurality of second optical fibers between a first position and a second position; and, a mirror configured to, as the plurality of second optical fibers is moving rotationally, convey light from exit faces of the plurality of first optical fibers to entrance faces of the plurality of second optical fibers. The plurality of second optical fibers can be contained in a housing which removabley attaches to the scanning device, and hence the plurality of second optical fibers and the housing can be interchanged and/or disposable. As the plurality of second optical fibers is moved rotationally, a larger area of tissue sample can be scanned as compared to scanning using a single OCT optical fiber.

Hence, an aspect of the specification provides a multi-channel OCT (Optical Coherence Tomography) probe, comprising: a plurality of first optical fibers optically connectable to an OCT light source; a plurality of second optical fibers different from the plurality of first optical fibers; a scanning device comprising: an actuator configured to rotationally move the plurality of second optical fibers between a first position and a second position, relative to the plurality of first optical fibers; and, a mirror configured to, as the plurality of second optical fibers is moving rotationally, convey light from exit faces of the plurality of first optical fibers to entrance faces of the plurality of second optical fibers; and, a housing containing the plurality of second optical fibers.

The multi-channel OCT probe can further comprise at least one GRIN (graded index) lens between the exit faces of the plurality of first optical fibers and the mirror, the at least one GRIN lens configured to focus the light from the exit faces of the plurality of first optical fibers onto the mirror.

The multi-channel OCT probe can further comprise at least one GRIN (graded index) lens between the mirror and the entrance faces of the plurality of second optical fibers, the at least one GRIN lens configured to focus the light from the mirror onto the entrance faces of the plurality of second optical fibers.

The multi-channel OCT probe can further comprise at least one GRIN (graded index) lens located at respective exit ends of the plurality of second optical fibers, the at least one GRIN lens configured to focus the light exiting the respective exit ends.

The actuator can comprise a galvanometer.

The actuator can be further configured to rotationally move the mirror with the plurality of second optical fibers.

Each of the plurality of second optical fibers can comprise a single-mode optical fiber.

Each of the plurality of second optical fibers can comprise a multi-core optical fiber.

The plurality of second optical fibers can comprise an optical fiber bundle.

The multi-channel OCT probe can further comprise an optical coupler configured to couple exit ends of the plurality of first optical fibers to the scanning device.

At least the housing and the plurality of second optical fibers can be disposable.

At least the housing and the plurality of second optical fibers can be removable from the scanning device.

Another aspect of the specification provides a system comprising: a multi-channel OCT (Optical Coherence Tomography) probe, comprising: a plurality of first optical fibers optically connectable to an OCT light source; a plurality of second optical fibers different from the plurality of first optical fibers; a scanning device comprising: an actuator configured to rotationally move the plurality of second optical fibers between a first position and a second position, relative to the plurality of first optical fibers; and, a mirror configured to, as the plurality of second optical fibers is moving rotationally, convey light from exit faces of the plurality of first optical fibers to entrance faces of the plurality of second optical fibers; and, a housing containing the plurality of second optical fibers; and, one or more of a computing device, a processor and a controller, configured to control at least the actuator.

The system can further comprise the OCT light source.

BRIEF DESCRIPTIONS OF THE DRAWINGS

For a better understanding of the various implementations described herein and to show more clearly how they may be carried into effect, reference will now be made, by way of example only, to the accompanying drawings in which:

FIG. 12 depicts optical components of an OCT probe that includes GRIN (graded index) lenses, for use in a medical procedure, according to non-limiting implementations.

DETAILED DESCRIPTION

Various implementations and aspects of the specification will be described with reference to details discussed below.

The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

The systems and methods described herein may be useful in the field of neurosurgery, including oncological care, neurodegenerative disease, stroke, brain trauma and orthopedic surgery; however persons of skill will appreciate the ability to extend these concepts to other conditions or fields of medicine. It should be noted that the surgical process is applicable to surgical procedures for brain, spine, knee and any other suitable region of the body.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

Figure 1:
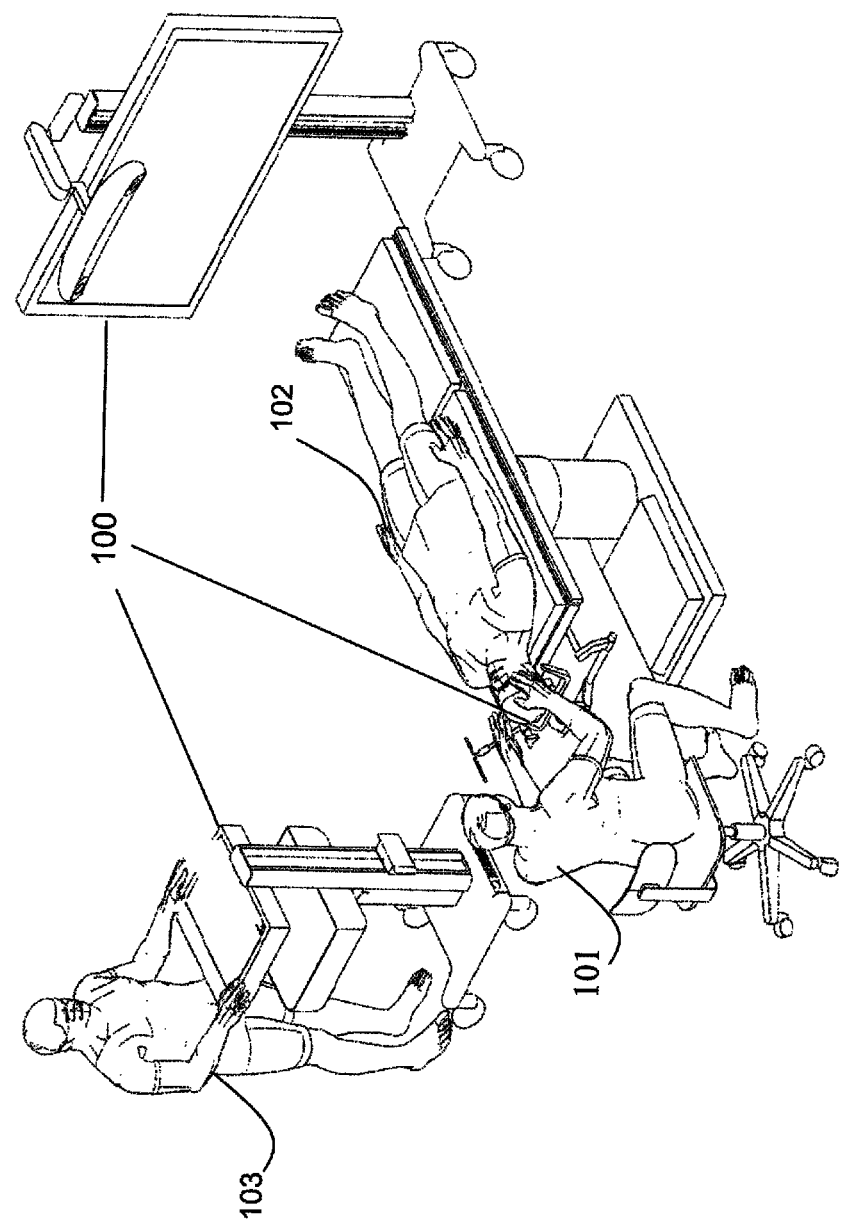
FIG. 1 shows an example operating room setup for a minimally invasive access port-based medical procedure, according to non-limiting implementations.

Referring to FIG. 1, a non-limiting example navigation system 100 is shown to support minimally invasive access port-based surgery or surgical corridor-based surgery. In FIG. 1, a neurosurgeon 101 conducts a minimally invasive port-based surgery on a patient 102 in an operating room (OR) environment. The navigation system 100 includes an equipment tower, tracking system, displays and tracked instruments to assist the surgeon 101 during the procedure. An operator 103 may also be present to operate, control and provide assistance for the navigation system 100.

Figure 2:
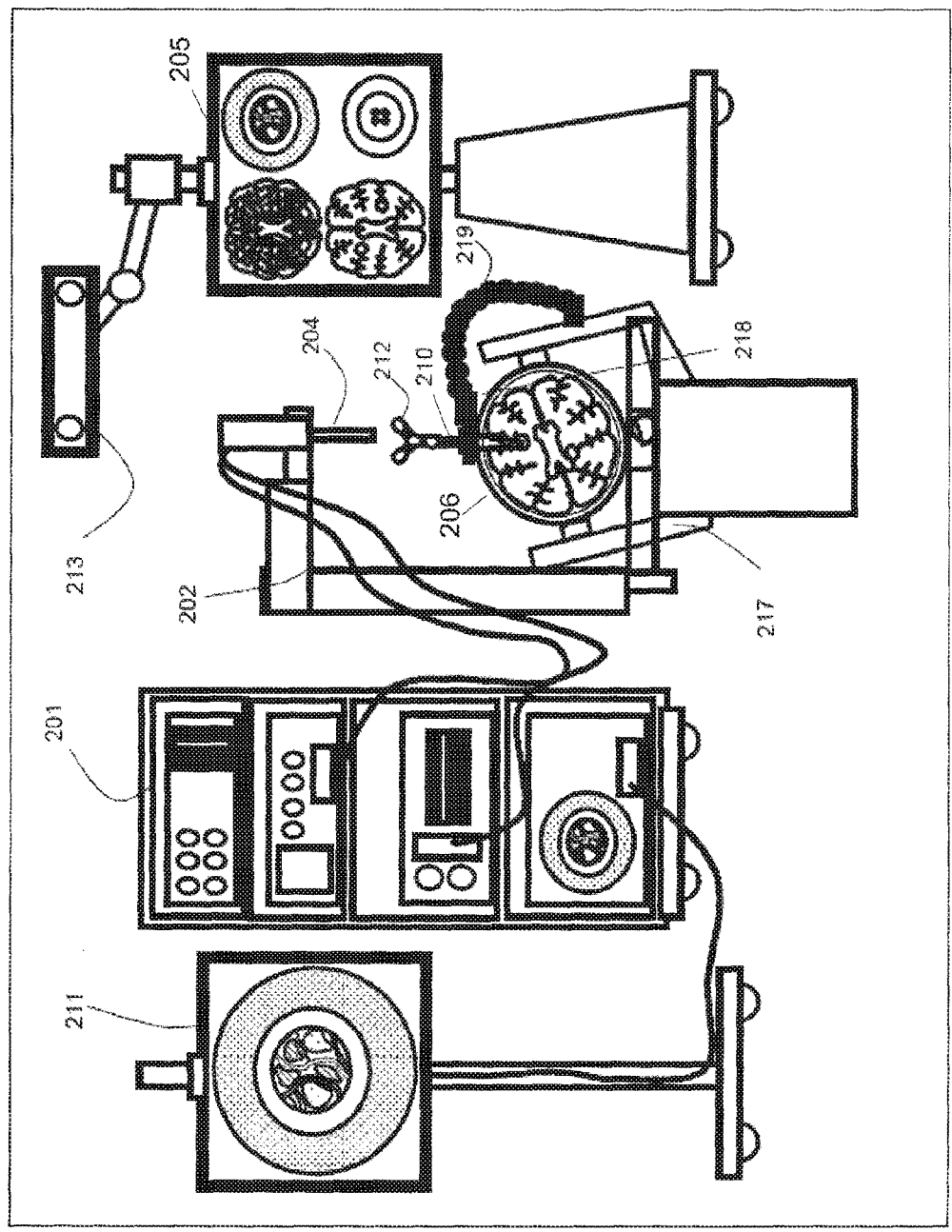
FIG. 2 is a block diagram illustrating components of a medical navigation system that may be used to implement a surgical plan for a minimally invasive surgical procedure, according to non-limiting implementations.

Referring to FIG. 2, a block diagram is shown illustrating components of an example medical navigation system 200, according to non-limiting implementations. The Medical navigation system 200 illustrates a context in which a surgical plan including equipment (e.g., tool and material) tracking, such as that described herein, may be implemented. The medical navigation system 200 includes, but is not limited to, one or more monitors 205, 211 for displaying a video image, an equipment tower 201, and a mechanical arm 202, which supports an optical scope 204. The equipment tower 201 may be mounted on a frame (e.g., a rack or cart) and may contain a computer or controller (examples provided with reference to FIGS. 3 and 6 below), planning software, navigation software, a power supply and software to manage the mechanical arm 202, and tracked instruments. In one example non-limiting implementation, the equipment tower 201 may comprise a single tower configuration with dual display monitors 211, 205, however other configurations may also exist (e.g., dual tower, single display, etc.). Furthermore, the equipment tower 201 may also be configured with a universal power supply (UPS) to provide for emergency power, in addition to a regular AC adapter power supply.

A patient's anatomy may be held in place by a holder. For example, in a neurosurgical procedure the patient's head may be held in place by a head holder 217, and an access port 206 and an introducer 210 may be inserted into the patient's head. The introducer 210 may be tracked using a tracking camera 213, which provides position information for the navigation system 200. The tracking camera 213 may also be used to track tools and/or materials used in the surgery, as described in more detail below. In one example non-limiting implementation, the tracking camera 213 may comprise a 3D (three-dimensional) optical tracking stereo camera, similar to one made by Northern Digital Imaging (NDI), configured to locate reflective sphere tracking markers 212 in 3D space. In another example, the tracking camera 213 may comprise a magnetic camera, such as a field transmitter, where receiver coils are used to locate objects in 3D space, as is also known in the art. Location data of the mechanical arm 202 and access port 206 may be determined by the tracking camera 213 by detection of tracking markers 212 placed on these tools, for example the introducer 210 and associated pointing tools. Tracking markers may also be placed on surgical tools or materials to be tracked. The secondary display 205 may provide output of the tracking camera 213. In one example non-limiting implementation, the output may be shown in axial, sagittal and coronal views as part of a multi-view display.

As noted above with reference to FIG. 2, the introducer 210 may include tracking markers 212 for tracking. The tracking markers 212 may comprise reflective spheres in the case of an optical tracking system and/or pick-up coils in the case of an electromagnetic tracking system. The tracking markers 212 may be detected by the tracking camera 213 and their respective positions are inferred by the tracking software.

As shown in FIG. 2, a guide clamp 218 (or more generally a guide) for holding the access port 206 may be provided. The guide clamp 218 may optionally engage and disengage with the access port 206 without needing to remove the access port 206 from the patient. In some examples, the access port 206 may be moveable relative to the guide clamp 218, while in the guide clamp 218. For example, the access port 206 may be able to slide up and down (e.g., along the longitudinal axis of the access port 206) relative to the guide clamp 218 while the guide clamp 218 is in a closed position. A locking mechanism may be attached to or integrated, with the guide clamp 218, and may optionally be actuatable with one hand, as described further below. Furthermore, an articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g., on another patient support, such as on the surgical bed), to ensure that when locked in place, the guide clamp 218 does not move relative to the patient's head.

Figure 3:
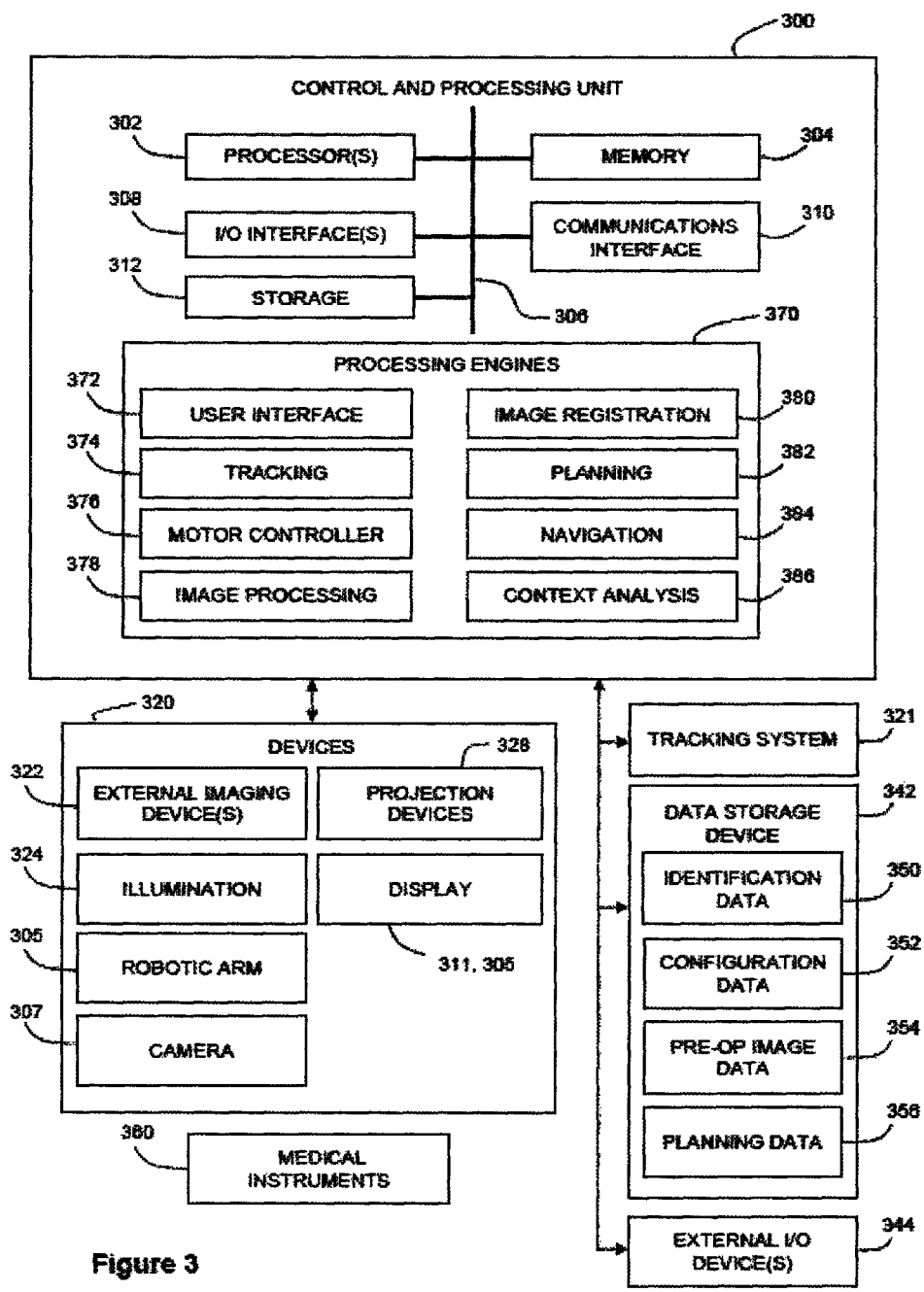
FIG. 3 depicts a block diagram illustrating components of a planning system used to plan a medical procedure that may then be implemented using the navigation system of FIG. 2, according to non-limiting implementations.

Referring to FIG. 3, a block diagram is shown illustrating a control and processing unit 300 that may be used in the navigation system 200 of FIG. 2 (e.g., as part of the equipment tower). In one example non-limiting implementation, control and processing unit 300 may include one or more processors 302, a memory 304, a system bus 306, one or more input/output interfaces 308, a communications interface 310, and storage device 312. In particular, one or more processors 302 may comprise one or more hardware processors and/or one or more microprocessors. Control and processing unit 300 may be interfaced with other external devices, such as tracking system 321, data storage device 342, and external user input and output devices 344, which may include, but is not limited to, one or more of a display, keyboard, mouse, foot pedal, and microphone and speaker. Data storage device 342 may comprise any suitable data storage device, including, but not limited to a local and/or remote computing device (e.g. a computer, hard drive, digital media device, and/or server) having a database stored thereon. In the example shown in FIG. 3, data storage device 342 includes, but is not limited to, identification data 350 for identifying one or more medical instruments 360 and configuration data 352 that associates customized configuration parameters with one or more medical instruments 360. Data storage device 342 may also include, but is not limited to, preoperative image data 354 and/or medical procedure planning data 356. Although data storage device 342 is shown as a single device in FIG. 3, in other implementations, data storage device 342 may be provided as multiple storage devices.

Medical instruments 360 may be identifiable using control and processing unit 300. Medical instruments 360 may be connected to and controlled by control and processing unit 300, and/or medical instruments 360 may be operated and/or otherwise employed independent of control and processing unit 300. Tracking system 321 may be employed to track one or more of medical instruments 360 and spatially register the one or more tracked medical instruments 360 to an intraoperative reference frame. In another example, a sheath may be placed over a medical instrument 360 and the sheath may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include, but are not limited, one or more external imaging devices 322, one or more illumination devices 324, a robotic arm, one or more projection devices 328, and one or more displays 305, 311.

Aspects of the specification may be implemented via processor(s) 302 and/or memory 304. For example, the functionalities described herein may be partially implemented via hardware logic in processor 302 and partially using the instructions stored in memory 304, as one or more processing modules 370 and/or processing engines. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example non-limiting implementation the processing modules 370 may be stored in the memory 304 and the processing modules may be collectively referred to as processing modules 370.

It is to be understood that the system is not intended to be limited to the components shown in FIG. 3. One or more components of the control and processing unit 300 may be provided as an external component or device. In one example non-limiting implementation, navigation engine 384 may be provided as an external navigation system that is integrated with control and processing unit 300.

Some implementations may be implemented using processor 302 without additional instructions stored in memory 304. Some implementations may be implemented using the instructions stored in memory 304 for execution by one or more general purpose microprocessors. Thus, the specification is not limited to a specific configuration of hardware and/or software.

While some implementations may be implemented in fully functioning computers and computer systems, various implementations are capable of being distributed as a computing product in a variety of forms and are capable of being applied regardless of the particular type of machine or computer readable media used to actually effect the distribution.

At least some aspects disclosed may be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache and/or a remote storage device.

A computer readable storage medium, and/or a non-transitory computer readable storage medium, may be used to store software and data which, when executed by a data processing system, causes the system to perform various methods. The executable software and data may be stored in various places including for example ROM, volatile RAM, nonvolatile memory and/or cache. Portions of this software and/or data may be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical and/or other forms of propagated signals, such as carrier waves, infrared signals, digital signals, and the like. The storage medium may comprise the internet cloud, storage media therein, and/or a computer readable storage medium and/or a non-transitory computer readable storage medium, including, but not limited to, a disc.

At least some of the methods described herein are capable of being distributed a computer program product comprising a computer readable medium that bears computer usable instructions for execution by one or more processors, to perform aspects of the methods described. The medium may be provided in various forms such as, but not limited to, one or more diskettes, compact disks, tapes, chips, USB (Universal Serial Bus) keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 200, which may include control and processing unit 300, is to provide tools to a surgeon and/or a neurosurgeon that will lead to the most informed, least damaging neurosurgical operations. In addition to removal of brain tumours and intracranial hemorrhages (ICH), the navigation system 200 may also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present specification may be applied to other suitable medical procedures.

Figure 4:
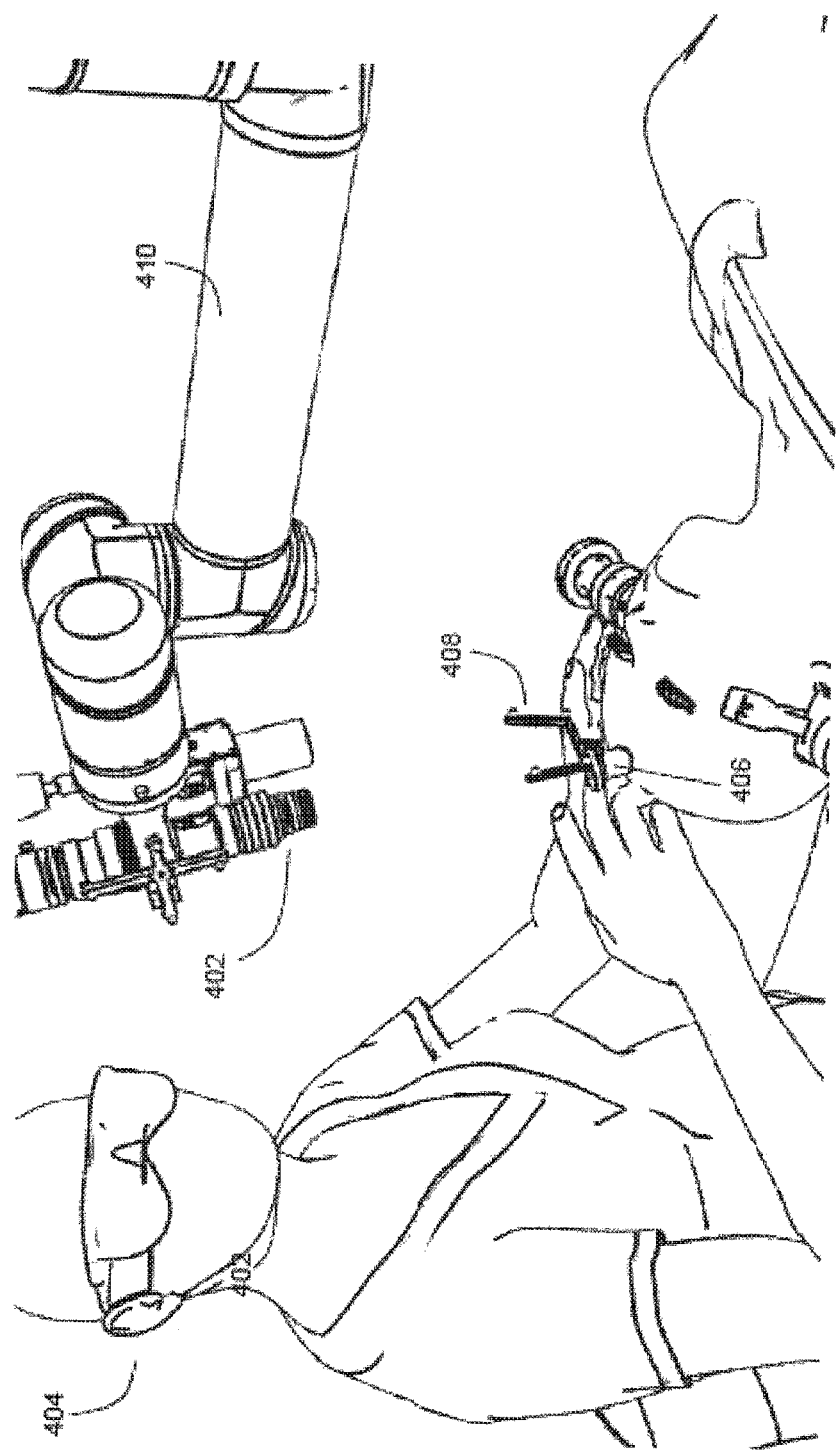
FIG. 4 depicts an example implementation port based brain surgery using a video scope, according to non-limiting implementations.

Attention is next directed to FIG. 4 which depicts a non-limiting example of a port-based brain surgery procedure using a video scope. In FIG. 4, operator 404, for example a surgeon, may align video scope 402 to peer down port 406. Video scope 402 may be attached to an adjustable mechanical arm 410. Port 406 may have a tracking tool 408 attached to it where tracking tool 408 is tracked by a tracking camera of a navigation system.

Even though the video scope 402 may comprise an endoscope and/or a microscope, these devices introduce optical and ergonomic limitations when the surgical procedure is conducted over a confined space and conducted over a prolonged period such as the case with minimally invasive brain surgery.

Figure 5:
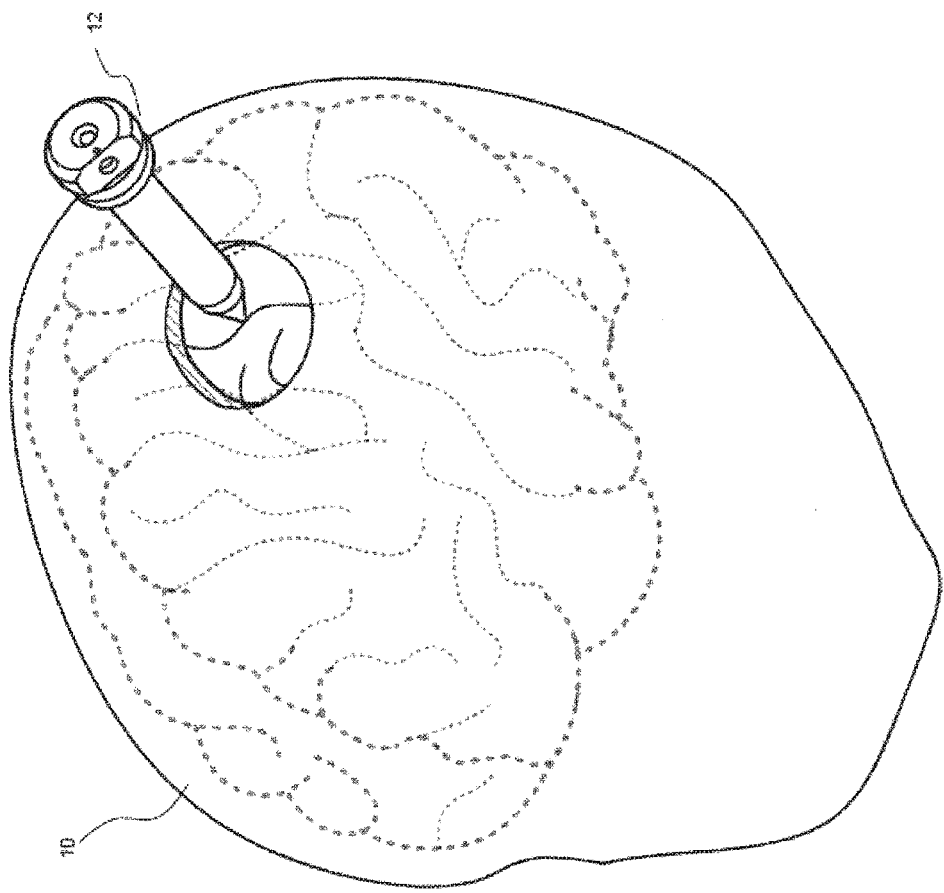
FIG. 5 depicts insertion of an access port into a human brain, for providing access to interior brain tissue during a medical procedure, according to non-limiting implementations.

FIG. 5 illustrates the insertion of an access port 12 into a human brain 10, in order to provide access to interior brain tissue during a medical procedure. In FIG. 5, access port 12 is inserted into a human brain 10, providing access to interior brain tissue. Access port 12 may include, but is not limited to, instruments such as catheters, surgical probes, and/or cylindrical ports such as the NICO BrainPath. Surgical tools and instruments may then be inserted within a lumen of the access port 12 in order to perform surgical, diagnostic or therapeutic procedures, such as resecting tumors as necessary. However, the present specification applies equally well to catheters, DBS needles, a biopsy procedure, and also to biopsies and/or catheters in other medical procedures performed on other parts of the body.

In the example of a port-based surgery, a straight and/or linear access port 12 is typically guided down a sulci path of the brain. Surgical instruments and/or surgical tools would then be inserted down the access port 12.

Figure 6:
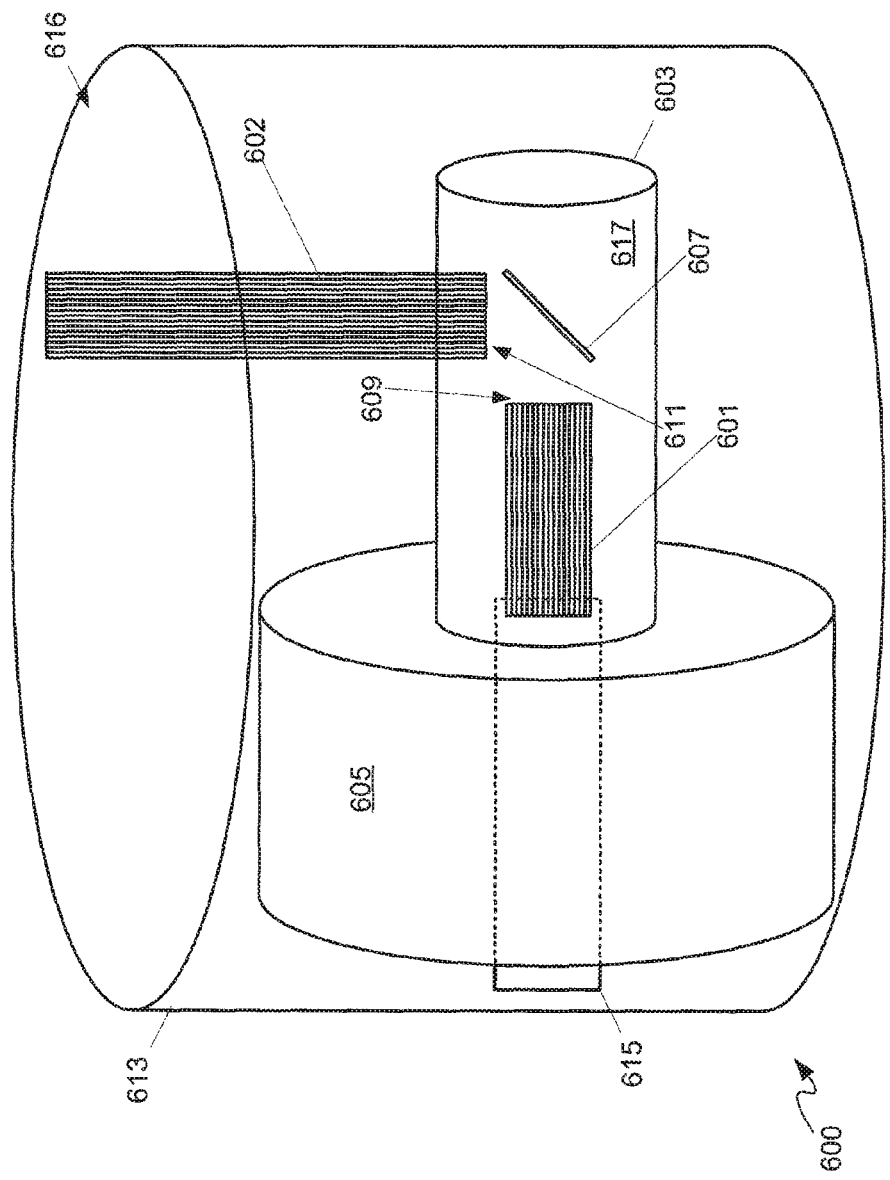
FIG. 6 depicts a multi-channel OCT (Optical Coherence Tomography) probe, for use in a medical procedure, according to non-limiting implementations.

Attention is next directed to FIG. 6, which depicts an example of a surgical tool that could be used with and/or in place of access port 12.

Specifically, FIG. 6 depicts a multi-channel OCT (Optical Coherence Tomography) probe 600 (interchangeably referred to hereafter as probe 600), comprising: a plurality of first optical fibers 601 optically connectable to an OCT light source (not depicted); a plurality of second optical fibers 602 different from plurality of first optical fibers 601; a scanning device 603 comprising: an actuator 605 configured to rotationally move plurality of second optical fibers 602 between a first position and a second position, relative to the plurality of first optical fibers 601; and, a mirror 607 configured to, as plurality of second optical fibers 602 is moving rotationally, convey light from exit faces 609 of plurality of first optical fibers 601 to entrance faces 611 of plurality of second optical fibers 602; and, a housing 613 containing plurality of second optical fibers 602. Plurality of first optical fibers 601 will be interchangeably referred to hereafter as fibers 601 and generically as a fiber 601. Plurality of second optical fibers 602 will be interchangeably referred to hereafter as fibers 602 and generically as a fiber 602. As depicted, probe 600 further comprises an optical coupler 615 connected to ends of fibers 601 opposite mirror 607, which enables connecting of fibers 601 to an OCT light source. However, probe 600 can be provided without optical coupler 615 and other devices for connecting fibers 601 to an OCT light source are within the scope of present implementations.

Furthermore, a distal end 616 of housing 613 is one or more of optically transparent and/or open and/or configured to transmit and receive OCT light. Hence, OCT light exiting fibers 602 also exits housing 613 at distal end 616, and OCT light scattered by a tissue sample, located at distal end 616, can enter distal end 616 and hence can also enter fibers 602. Furthermore, many components of probe 600 are contained within housing 613, and hence housing 613 is depicted as being at least partially transparent in FIG. 6, though housing 613 generally is not transparent, other than at distal end 616.

As depicted, scanning device 603 further comprises a second housing 617 containing fibers 602 and mirror 607. As such, it is understood that fibers 602 and mirror 607 depicted in FIG. 6 are contained within housing 617, and hence housing 617 is depicted as being at least partially transparent in FIG. 6, though housing 617 generally is not transparent.

Mirror 607 can comprise one or more of a silvered mirror, polished metal, a dichroic mirror, a prism, and the like. Furthermore, while mirror 607 is depicted in profile as flat, any shape of mirror 607 can conveys light between fibers 601, 602 is within the scope of present implementations, In some implementations, as depicted, actuator 605 comprises a galvanometer. Hence, while not depicted, actuator 605 can be connected to a power supply configured to power the galvanometer. Alternatively, actuator 605 can comprise one or more of a rotational motor and/or a stepper motor.

Figure 7:
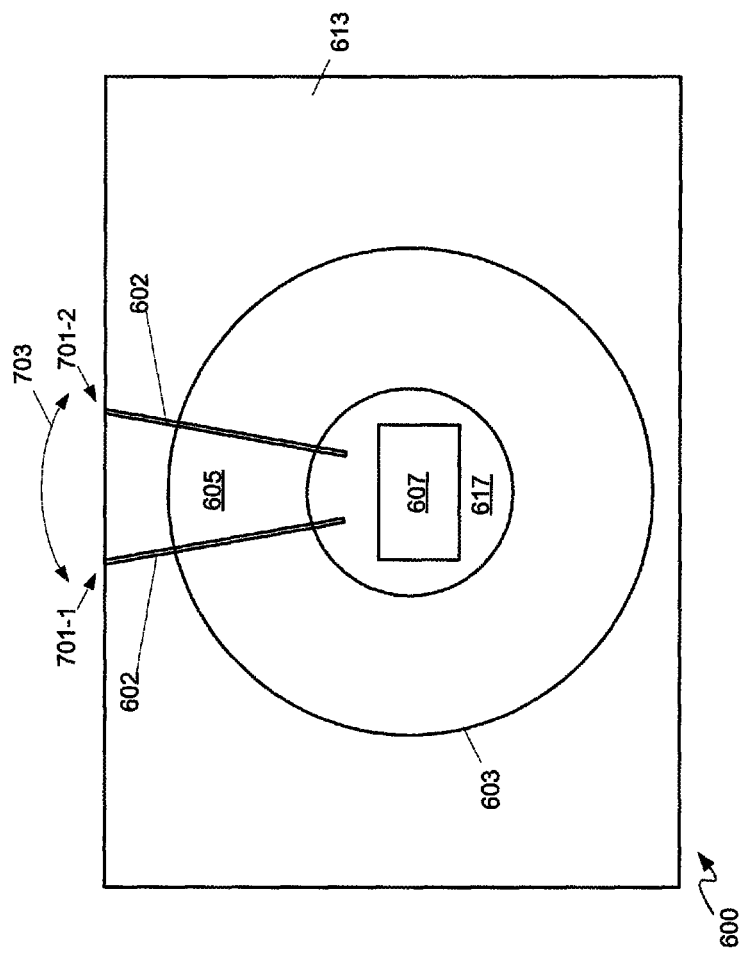
FIG. 7 depicts front perspective view of the probe of FIG. 6, with a fiber array rotating between two positions, according to non-limiting implementations.

Attention is next directed to FIG. 7, which depicts a front view of probe 600, with fibers 602 and scanning device 603 being visible inside housing 613 for clarity. While not all components of probe 600 are depicted in FIG. 7, they are nonetheless appreciated to be present. Furthermore, a general position of mirror 607 is indicated, though it is appreciated that mirror 607 is located internal to housing 617.

In particular, FIG. 7 depicts fibers 602, being rotated between a first position 701-1 and a second position 701-2, with rotation there between indicated using arrow 703. First position 701-1 and second position 701-2 will be interchangeably referred to hereafter, collectively, as positions 701, and generically as a position 701. While positions 701 are depicted as being about 20° from each other, other rotational distances between positions 701 are within the scope of present implementations; furthermore, the rotational distance between positions 701 can be controlled and/or tuned using a computing device and/or processor in communication with scanning device 603.

Hence, actuator 605 generally rotates housing 617, which in turn rotates fibers 602, and mirror 607 reflect OCT light from fibers 601 into fibers 602 independent of a position of fibers 602. A position of fibers 601 is generally fixed relative to actuator 605. In some implementations mirror 607 is fixed relative to actuator 605 while in other implementations actuator 605 is further configured to rotationally move mirror 607 with plurality of second optical fibers 602 to facilitate conveying of OCT light between fibers 601 and fibers 602.

FIGS. 6 and 7 further depict a position of housing 613 relative to housing 617. In particular, each of housings 613, 617 can be cylindrical, and housing 613, as depicted, is positioned to contain housing 617 and scanning device 603, as well as fibers 602. Furthermore, housing 613 and fibers 602 can be provided as a disposable and or removable unit of probe 600.

Figure 8:
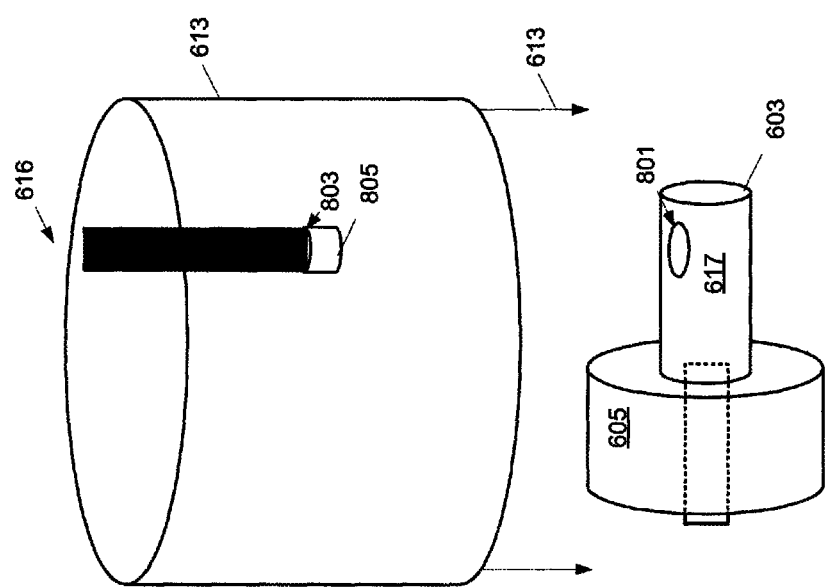
FIG. 8 depicts the probe of FIG. 6 in disassembled state, according to non-limiting implementations.

For example, with reference to FIG. 8, which depicts probe 600 in a disassembled state, according to some implementations, housing 617 can comprise a hole 801, and an end 803 of fibers 602, opposite distal end 616, can comprise a connector 805 that mates with hole 801 such that fibers 602 can easily be mated housing 617. In such implementations, it is appreciated that housing 613 is configured to slide over and/or snap into and/or mate with scanning device 603 in a manner that enables housing 613 to house scanning device 603 while further enabling fibers 602 to mate with housing 617 and rotate therewith. Hence, and end of housing 613 opposite distal end 616 can be one or more of open, temporarily open, and configured to slide over scanning device 603. Furthermore, fibers 602 can be connected to housing 613 in a manner that enables fibers 602 to rotate therein, as described above with respect to FIG. 7, using any combination of suitable mounting devices.

However any components that can be used to removabley connect fibers 602 and housing 613 to scanning device 603 are within the scope of present implementations. Indeed, FIG. 8 shows that housing 613 and fibers 602 contained therein, are removable from probe 600 and hence can be one or more interchangeable and disposable. Indeed, by providing scanning device 603 with mirror 607 and fibers 601, along with housing 617, interchangeability and/or disposability of fibers 602 and housing 613 are enabled. Hence, fibers 602 and housing 613 can be removed from probe 600 and cleaned after use and/or fibers 602 and housing 613 can be disposed and replaced with new fibers 602 and housing 613.

Furthermore, as housing 613 and fibers 602 are generally disposable, and/or removable, different housings 613 and different fibers 602 of different configurations van be provided, including, but not limited to, different fiber lengths (e.g. different scanning area), different focal lengths, and different beam sizes, and the like.

In yet further implementations, probe 600 can comprise yet a further housing that contains fibers 602 that in turn mates with hole 801, the further housing rotated by housing 617, which in turn rotates fibers 602.

Returning to FIGS. 6 and 7, a particular configuration of fibers 602 are depicted. For example, as can be seen in FIG. 6, fibers 602 are arranged side-by-side and/or in a planar configuration and/or flat and/or in a two-dimensional array, and a side view of an edge of such a plane and/or array shown in FIG. 6. Hence, fibers 602 extend radially along a longitudinal axis of housing 617 and/or fibers 602 are arranged radially, side-by-side along a longitudinal axis of housing 617, defining an illumination edge of fibers 602 between fibers 602 located at opposite sides of the plane and/or the array. Hence, as fibers 602 move between positions 701, fibers 602 sweep out lines and/or traces of illumination of OCT light onto a tissue sample and the like, which result in an area of the tissue sample being illuminated with OCT light that has: a width similar to the length of an illumination edge of fibers 602; and a length defined by positions 701. In other words, at each position 701, fibers 602 illuminate a respective line and/or trace of a tissue sample and as fibers 602 move between positions 701, areas of a tissue sample there between are also illuminated.

Furthermore, fibers 601, 602 and mirror 607 are arranged so that mirror 607 conveys OCT light between fibers 601, 602. Hence, fibers 601 are also arranged side-by-side and/or in a planar configuration and/or flat and/or in a two-dimensional array, but within housing 617 and relative to mirror 607 so that mirror 607 conveys OCT light between fibers 601, 602.

Furthermore, fibers 602 can be attached to housing 613 using any suitable combination of mounting devices, and the like, indeed, the positions of fibers 602 within housing and positions anchor configurations of connection devices for removabley connect housing 613 to scanning device 603 are selected such that, when housing 613 is attached to scanning device 603, fibers 602 both extend radially along a longitudinal axis of housing 617, as described above, and are positioned relative to mirror 607 such that mirror 607 conveys OCT light between fibers 601, 602.

Figure 9:
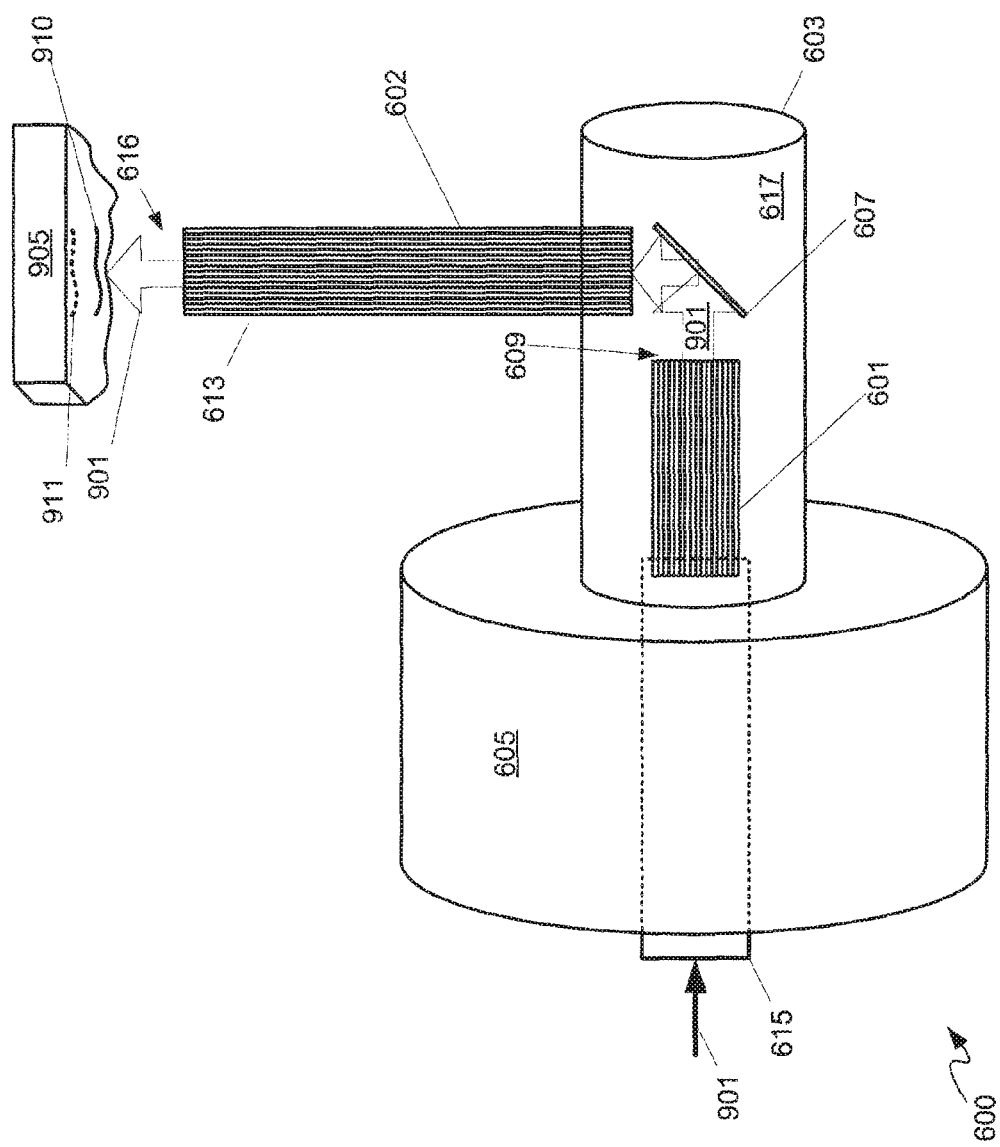
FIG. 9 depicts the probe of FIG. 6 in operation, according to non-limiting implementations.

Attention is next directed to FIG. 9, which us substantially similar to FIG. 6, with like elements having like numbers, and depicts probe 600 in operation at a given position to scan a tissue sample 905. However, in FIG. 9, probe 600 is depicted without housing 613 for clarity, but housing 613 is assumed to be nonetheless present.

In FIG. 9, OCT light 901 is depicted as entering optical coupler 615, for example from an OCT light source, with OCT light 901 conveyed to fibers 601 by optical coupler 615. When OCT light 901 exits fibers 601, OCT light 901 is spread out over an area defined by exit faces 609 of fibers 601; hence, optical coupler 615 is generally configured to spread OCT light 901 across entrance faces of each of fibers 601 (the entrance faces being opposite exit faces 609), such that OCT light 901 exits exit faces of fibers 601, reflects from mirror 607, and enters entrance faces 611 of fibers 602. Fibers 602 convey' OCT light 901 to tissue sample 905, which illuminate a line and/or trace 910 on tissue sample 905. A shape of trace 910 can reflect a surface topology of tissue sample 905.

In particular, trace 910 can occur at one of positions 701 and when fibers 602 move to the other of positions 701, a fibers 602 can illuminate a trace 911, such that an area between traces 910, 911 are illuminated with OCT light.

In other words, as fibers 602 are illuminating trace 910 (which is larger than a point, as would occur with a single fiber illuminating tissue sample 905), and as fibers 602 are moving rotationally, an area of tissue sample 905 between traces 910, 911 is illuminated with OCT light 901, and such an area is larger than would occur with a single fiber illuminating tissue sample 905. Indeed, with conventional single fiber scanning systems, only a single trace of OCT light would illuminate a tissue sample.

While not depicted, it is understood that fibers 602 also collect light from tissue sample 905, which is conveyed back through fibers 602, reflected from mirror 607 to fibers 601, and through connector 605 to an OCT interferometer for collection and analysis, for example by a computing device configured to process received OCT light as a function of position of fibers 602.

Figure 10:
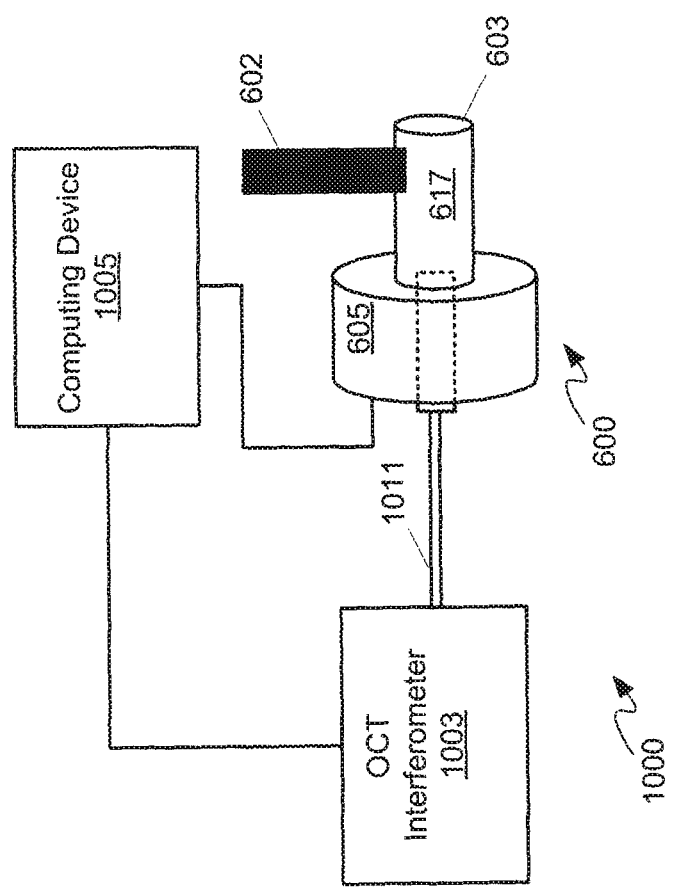
FIG. 10 depicts an OCT system that includes the probe of FIG. 6, according to non-limiting implementations.

For example, attention is directed to FIG. 10, which depicts a system 1000 that comprises probe 600, an OCT interferometer 1003 and a computing device 1005 which can comprise control and processing unit 300. While not all components of probe 600 are numbered and/or depicted, they are understood to be nonetheless present; in particular, probe 600 is depicted without housing 613 for clarity, but housing 613 is assumed to be nonetheless present.

In general, OCT interferometer 1003 is in communication with probe 600 via an optical fiber 1011, for example to provide OCT light to fibers 601 via optical coupler 615. Furthermore, computing device 1005 is configured to: receive and process OCT images from OCT interferometer 1003, as well as control a position of probe 600, for example by controlling a position scanning device 603 and/or a position actuator 605 and/or a position of fibers 602 to illuminate a sample and/or target with OCT light and collect OCT images therefrom. Hence, computing device 1005 can be provisioned with a look up table that correlates settings for scanning device 603 and/or actuator 605 with positions of fibers 602 so that a plurality OCT image traces can be received, for example at traces 910, 911 and traces there between, and processed from OCT interferometer 1003 to generate an image of the sample and/or target from the plurality OCT image traces based on the respective positions of fibers 602 at which each of the plurality OCT image traces was acquired.

Further details of a non-limiting prototype of probe 600 are now provided, where scanning device 603 comprises a galvanometer.

In particular the non-limiting prototype of probe 600 generally enhances OCT imaging speed for example in an endo-OCT imaging system, by combining the galvanometer, with a fiber probe having a planar profile, and the like, as described above. At least a portion of the non-limiting prototype of probe 600 was made disposable by providing housing 613 in the form of a hollow metal tube which hooks up with the galvanometer. Inside the hollow metal tube, a mirror (e.g. mirror 607) is used for coupling OCT light to fibers 602 also located inside the hollow metal tube. When the galvanometer is rotating, the fibers 602 rotate and scan a tissue sample in front of it. While not depicted, the non-limiting prototype of probe 600 includes a forwarding moving motor which can advance fibers 602 along a surface of a tissue sample. The disposable portion of the non-limiting prototype of probe 600 is mounted inside a tube housing for scanning protection. Hence, the disposable portion of the non-limiting prototype of probe 600 is passive and does not include the galvanometer or other electrical components. As such, the non-limiting prototype of probe 600 can be configured with different disposable portions of different configurations, including, but not limited to, different fiber lengths (e.g. different scanning area), different focal lengths, and different beam sizes, and the like. Each of the different disposable portions, when mated with the remainder of the non-limiting prototype of probe 600, hence uses the same scanning mechanism.

As described above, in the non-limiting prototype of probe 600, fibers 602 comprise a two-dimensional array of fibers. In some implementations of the non-limiting prototype of probe 600, each of fibers 602 comprise a single mode fiber (SMF) with having about a 9 μm core diameter, and about a 125 μm cladding diameter. Hence, a 10-channel probe (e.g. 10 single mode fibers aligned side-by-side lengthwise) will have a size of about 1.25 mm by about 0.125 mm, which are dimensions that are compatible with port-based surgical techniques.

Figure 11:
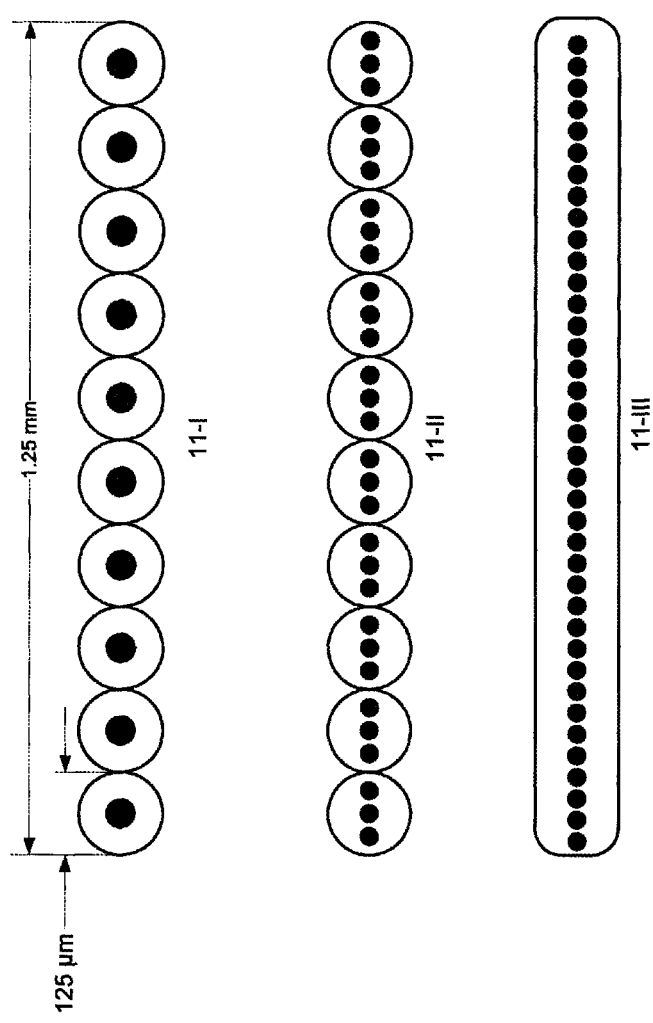
FIG. 11 depicts illumination end views of three different configurations of arrays of fibers for use in the probe of FIG. 6, according to non-limiting implementations.

An illumination end view of an example of such a 10-channel probe is depicted in FIG. 11, in view 11-I, where the width of the 10-channel probe is about 1.25 mm, assuming a diameter of each of 10 SMF is about 125 μm.

FIG. 11 further depicts an illumination end view of an example of such a higher-channel probe is depicted in view 11-II, where each fiber comprises a multi-core fiber. For example, as depicted, each of the multicore fibers comprises 3 cores inside one SMF cladding, with negligible cross talk or optical power coupling between cores. Hence, the probe depicted in view 11-II has a same size as the probe in view 11-I, but with 30 channels.

FIG. 11 further depicts an illumination end view of an example of another higher-channel probe is depicted in view 11-III, where the probe comprise a fiber bundle comprising a plurality of cores. Indeed, use of fiber bundles can achieve even higher channel capacity than individual multi-channel fibers, which can lead to real-time OCT scanning in an endo-OCT imaging system. Indeed, in some implementations, fiber bundles can be used to provide a 100-channel probe and higher.

Currently, the tuning speed of tunable laser used in high-speed swept source OCT system is around few tens of KHz (including, for example, 16 KHz systems). In the non-limiting prototype of probe 600 using a 100-channel configuration, having an imaging speed of 16 KHz, a 160 Hz tunable laser source can be used instead of a 16 KHz laser of prior art scanning systems. Such a lower speed tunable lasers generally have higher linearity, more stable tuning and lower cost over high speed laser of prior art scanning systems. Moreover, tunable semiconductor lasers are presently in the few hundreds HZ range and hence can be monolithically integrated with the presently described probes, which can lead to reducing one or more of size, weight, power and cost of OCT probes; for example, tunable semiconductor lasers are not generally used with prior art scanning systems as their speeds are too low, a problem that is mitigated with presently described OCT probes.

It is further appreciated that OCT probes described herein are not limited for use with endo-OCT systems. For example, scanning areas can be enlarged by using longer fibers and without involving large bulky optical lens, and hence OCT probes described herein can be adapted for use in real-time three-dimensional imaging systems for surface imaging.

It is further appreciated that light throughput between fibers 601, 602 can be enhanced using one or more GRIN (graded index) lenses. For example, attention is next directed to FIG. 12 which depicts components of an OCT probe 1200 similar to probe 600; depicted components include: an optical fiber 1201, and optical fiber 1202, and a mirror 607 configured to convey light between optical fiber 1202 and optical fiber 1202. For example, optical fiber 1201 can comprise a fiber in fibers 601, optical fiber 1202 can comprise a fiber in fibers 602, and mirror 1207 can comprise mirror 607. While other components of OCT probe 1200 are not depicted, they are appreciated to be nonetheless present.

Also depicted in FIG. 12 is a path of OCT light 1210 through OCT probe 1200; specifically, OCT light 1210 is conveyed through fiber 1201, reflected from mirror 1207 to fiber 1202, where OCT light 1210 exits at a distal end. OCT light 1210 is depicted as two arrows passing through probe 1200, and having a width and/or area defined by the distance between the two arrows.

In contrast to probe to probe 600, probe 1200 further comprises at least one GRIN lens 1220-1 between an exit face of optical fiber 1201 and mirror 1207, at least one GRIN lens 1220-1 configured to focus light 1210 from the exit faces of fiber 1201 onto mirror 1207. In other words, because GRIN lens 1220-1 has a graded index of refraction, light 1210 is focused as light 1210 passes through GRIN lens 1220-1, which is property of each of the GRIN lenses depicted in FIG. 12.

Furthermore, as depicted, probe 1200 further comprises at least one GRIN lens 1220-2 between mirror 1207 and an entrance face of fiber 1202, the at least one GRIN lens 1220-2 configured to focus light 1210 from mirror 1207 onto the entrance faces of fiber 1220-2.

Furthermore, as depicted, probe 1200 further comprises at least one GRIN lens 1220-3 between located at an exit end of fiber 1202, the at least one GRIN lens 1220-3 configured to focus light 1210 exiting the exit end, for example onto a tissue sample (not depicted).

While three GRIN lenses 1220-1, 1220-2, 1220-3 are depicted in FIG. 12, in other implementations a subset of GRIN lenses 1220-1, 1220-2, 1220-3 can be provided.

Furthermore, probe 600 can be adapted in a manner similar to probe 1200. Specifically, in some implementations, probe 600 can comprise at least one GRIN lens between the exit faces 609 of plurality of first optical fibers 601 and mirror 607, the at least one GRIN lens configured to focus OCT light from exit faces 609 of the plurality of first optical fibers 601 onto the mirror 607, similar to GRIN lens 1220-1. In some implementations, GRIN lenses can be provided for each of fibers 601, in a one-to-one relationship, while in other implementations one or more GRIN lenses can be used to focus light for two or more fibers 601.

Similarly, in some implementations, probe 600 can comprise at least one GRIN lens between mirror 607 and entrance faces 611 of the plurality of second optical fibers 602, the at least one GRIN lens configured to OCT focus the light from mirror 607 onto the entrance faces 611 of the plurality of second optical fibers 602, similar to GRIN lens 1220-2. In some implementations, GRIN lenses can be provided for each of fibers 602, in a one-to-one relationship, while in other implementations one or more GRIN lenses can be used to focus light for two or more fibers 602.

Similarly, in some implementations, probe 600 can comprise at least one GRIN lens located at respective exit ends of plurality of second optical fibers 602, the at least one GRIN lens configured to focus OCT light exiting the respective exit ends, similar to GRIN lens 1220-3. In some implementations, GRIN lenses can be provided for each of fibers 602, in a one-to-one relationship, while in other implementations one or more GRIN lenses can be used to focus light for two or more fibers 602.

Indeed, provided herein are OCT probes comprising one or more GRIN lenses respectively located at an entrance face or an exit face of respective optical fibers of the OCT probes, the GRIN lenses used to enhance light throughout through the OCT probes. Such GRIN lenses can be used with single fiber OCT probes, including, but not limited to, probe 1200 and multi-fiber OCT probes, including, but not limited to, probe 600. Use of such GRIN lenses generally mitigates issues with aligning various corresponding ends of fibers, for example alignment of exit faces 609 of fibers 601 and entrance faces 611 of fibers 602.

While features of OCT probes described with reference to specific implementations, features described with reference to one implementation of an OCT probe may be used with other implementations of OCT probes. For example, any of the OCT probes described herein may be adapted to include anti-reflective coatings, immersion materials, index matching materials, tracking devices, and the like.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A multi-channel OCT (Optical Coherence Tomography) probe, comprising:
 a plurality of first optical fibers configured to optically connect to an OCT light source, the plurality of first optical fibers arranged in a first two-dimensional array;
 a plurality of second optical fibers different from the plurality of first optical fibers, the plurality of second optical fibers arranged perpendicular to the plurality of first optical fibers, the plurality of second optical fibers arranged in a second two-dimensional array such that the plurality of second optical fibers extend radially and side-by-side along a longitudinal axis, and an illumination edge is defined by the plurality of second optical fibers located at opposite sides of the second two-dimensional array;
 a scanning device comprising:
  an actuator configured to rotationally move the plurality of second optical fibers, arranged in the second two-dimensional array, between a first position and a second position, relative to the plurality of first optical fibers, the illumination edge of the plurality of second optical fibers moving parallel to an axis of rotation, the longitudinal axis being perpendicular to the axis of rotation; and,
  a mirror located in an optical path between exit faces of the plurality of first optical fibers and entrance faces of the plurality of second optical fibers, the mirror configured to, as the plurality of second optical fibers is moving rotationally, convey light from the exit faces of the plurality of first optical fibers to the entrance faces of the plurality of second optical fibers; and,
 a housing containing the plurality of second optical fibers.

2. The multi-channel OCT probe of claim 1, further comprising at least one GRIN (graded index) lens between the exit faces of the plurality of first optical fibers and the mirror, the at least one GRIN lens configured to focus the light from the exit faces of the plurality of first optical fibers onto the mirror.

3. The multi-channel OCT probe of claim 1, further comprising at least one GRIN (graded index) lens between the mirror and the entrance faces of the plurality of second optical fibers, the at least one GRIN lens configured to focus the light from the mirror onto the entrance faces of the plurality of second optical fibers.

4. The multi-channel OCT probe of claim 1, further comprising at least one GRIN (graded index) lens located at respective exit faces of the plurality of second optical fibers, the at least one GRIN lens configured to focus the light exiting the respective exit faces.

5. The multi-channel OCT probe of claim 1, wherein the actuator comprises a galvanometer.

6. The multi-channel OCT probe of claim 1, wherein the actuator is further configured to rotationally move the mirror with the plurality of second optical fibers.

7. The multi-channel OCT probe of claim 1, wherein each of the plurality of second optical fibers comprises a single-mode optical fiber.

8. The multi-channel OCT probe of claim 1, wherein each of the plurality of second optical fibers comprises a multi-core optical fiber.

9. The multi-channel OCT probe of claim 1, wherein the plurality of second optical fibers comprises an optical fiber bundle.

10. The multi-channel OCT probe of claim 1, further comprising an optical coupler configured to couple the exit faces of the plurality of first optical fibers to the scanning device.

11. The multi-channel OCT probe of claim 1, wherein at least the housing and the plurality of second optical fibers are disposable.

12. The multi-channel OCT probe of claim 1, wherein at least the housing and the plurality of second optical fibers are removable from the scanning device.

13. A system comprising:
 a multi-channel OCT (Optical Coherence Tomography) probe, comprising: a plurality of first optical fibers configured to optically connect to an OCT light source, the plurality of first optical fibers arranged in a first two-dimensional array; a plurality of second optical fibers different from the plurality of first optical fibers, the plurality of second optical fibers arranged perpendicular to the plurality of first optical fibers, the plurality of second optical fibers arranged in a second two-dimensional array such that the plurality of second optical fibers extend radially and side-by-side along a longitudinal axis, and an illumination edge is defined by the plurality of second optical fibers located at opposite sides of the second two-dimensional array; a scanning device comprising: an actuator configured to rotationally move the plurality of second optical fibers, arranged in the second two-dimensional array, between a first position and a second position, relative to the plurality of first optical fibers, the illumination edge of the plurality of second optical fibers moving perpendicular to an axis of rotation, the longitudinal axis being parallel to the axis of rotation; and, a mirror located in an optical path between exit faces of the plurality of first optical fibers and entrance faces of the plurality of second optical fibers, the mirror configured to, as the plurality of second optical fibers is moving rotationally, convey light from the exit faces of the plurality of first optical fibers to the entrance faces of the plurality of second optical fibers; and, a housing containing the plurality of second optical fibers; and,
 one or more of a computing device, a processor and a controller, configured to control at least the actuator.

14. The system of claim 13, further comprising the OCT light source.

* * * * *